United States Patent [19]

Hughes

[11] 4,330,434
[45] May 18, 1982

[54] SUPPORTED ACIDIC CATALYST

[75] Inventor: O. Richard Hughes, Chatham, N.J.

[73] Assignee: Celanese Corporation, New York, N.Y.

[21] Appl. No.: 250,191

[22] Filed: Apr. 2, 1981

Related U.S. Application Data

[62] Division of Ser. No. 119,682, Feb. 8, 1980, Pat. No. 4,293,499.

[51] Int. Cl.³ .............................................. B01J 31/02
[52] U.S. Cl. ..................................... 252/430; 252/428
[58] Field of Search ................................ 252/428, 430

[56] References Cited

U.S. PATENT DOCUMENTS

| | | | |
|---|---|---|---|
| 2,224,809 | 12/1940 | Coleman | 560/247 |
| 2,816,887 | 12/1957 | Lamborn | 252/428 |
| 3,922,294 | 11/1975 | Lenpold et al. | 560/247 |
| 3,932,306 | 1/1976 | Rona | 560/247 |
| 3,976,595 | 8/1976 | Scott et al. | 252/428 |
| 4,128,727 | 12/1978 | Lenpold et al. | 560/247 |

Primary Examiner—John F. Niebling
Attorney, Agent, or Firm—Charles B. Barris

[57] ABSTRACT

This invention provides a process for producing a carboxylate ester from a monoolefin and a carboxylic acid, in the presence of a solid catalyst comprising a composite of 5-sulfoisophthalic acid and a carrier substrate having a surface area between about 1–1000 m²/gram.

A carboxylate ester such as ethyl propionate is produced with a STY efficiency of at least 100 grams/liter hour.

4 Claims, No Drawings

SUPPORTED ACIDIC CATALYST

This is a division of application Ser. No. 119,682, filed Feb. 8, 1980, now U.S. Pat. No. 4,293,499.

BACKGROUND OF THE INVENTION

The use of acidic materials as catalysts in chemical reactions is well known in the prior art. Illustrative of chemical conversions which are acid-catalyzed are the production of alcohols by the hydration of olefins, the production of esters by the interaction of carboxylic acids with olefins, the production of ethers by dehydration of alcohols or by the reaction of alcohols with olefins, the alkylation of aromatic hydrocarbons, the cracking of gas oil, the polymerization of olefins, the isomerization of hydrocarbons, and the like.

Among the catalysts employed for acid catalysis are mineral acids, heteropoly acids and ion exchange resins. Catalysts which are known for the esterification of olefins with carboxylic acids include silica-alumina and other various mixtures of refractory metal oxides. The activity of metal oxide catalysts usually is promoted by acid pretreatment of the catalysts.

U.S. Pat. No. 2,174,985 discloses a process for the esterification of olefins in vapor phase in the presence of a heteropoly acid catalyst such as phosphotungstic acid supported on activated alumina.

U.S. Pat. No. 3,053,887 discloses a method for esterification of isoolefins at a temperature below about 5° C. in the presence of a catalyst consisting of a sulfonated copolymer of styrene crosslinked with divinylbenzene.

U.S. Pat. No. 3,492,341 describes a process for the esterification of monoolefins with carboxylic acids at 100°–800° C. in the presence of a mordenite type crystalline aluminosilicate catalyst predominantly in the hydrogen form.

U.S. Pat. No. 3,922,294 describes a gas/liquid phase process for the manufacture of isopropyl esters which involves passing propylene and a carboxylic acid continuously in parallel flow over an acid ion exchanger of the sulfonic acid type. The service life of the catalyst is improved by the addition of a strong mineral acid to the liquid phase.

U.S. Pat. No. 3,920,582 and 3,932,306 describe two related types of solid catalysts for heterogeneous reactions such as hydration of olefins, esterification of olefins, and the like. One type of catalyst is a composite consisting of a solid carrier and an acidic compound containing at least two sulfonic groups per molecule. The other type of catalyst is a composite consisting of a solid carrier and carboxymethane sulfonic acid.

U.S. Pat. No. 4,011,272 describes a process for producing tertiary butyl alcohol which involves reacting isobutylene with an aqueous organic acid solution in the presence of an acidic ion exchange resin.

There has been continuing development effort to overcome the many difficulties characteristic of acid catalyzed synthesis methods. It is well known that acid catalysts are highly corrosive to processing equipment, and that the cumulation of metal ions resulting from the corrosion has a deactivating effect on the catalyst. In reactions involving olefins there is the problem of undesirable olefin polymerization side reactions which lower the overall efficiency of the processes, and which have the additional disadvantages of contaminating and deactivating the acid catalysts and complicating reaction product recovery procedures.

There remains a need for improved methods and catalysts for overcoming the difficulties and inefficiencies of acid catalyzed processes.

Accordingly, it is an object of this invention to provide a novel strongly acidic solid catalyst which exhibits long term stability and reactivity under acid catalyzed heterogeneous reaction conditions.

It is another object of this invention to provide a strongly acidic solid catalyst which is highly selective for the production of esters by the reaction of olefins with carboxylic acids.

It is a further object of this invention to provide an improved process for the esterification of an olefin with a carboxylic acid, wherein the conversion selectivity of the carboxylic acid to ester product is substantially quantitative under optimal conditions.

Other objects and advantages of the present invention shall become apparent from the accompanying description and examples.

DESCRIPTION OF THE INVENTION

One or more objects of the present invention are accomplished by the provision of a strongly acidic solid catalyst composition comprising a composite of between about 0.5–40 weight percent, based on catalyst weight, of 5-sulfoisophthalic acid in combination with a carrier substrate having a surface area between about 1–1000 $m^2$/gram.

The catalyst composition can be prepared by the simple expediency of dissolving the 5-sulfoisophthalic acid component in an aqueous medium, preferably an aqueous alkanol medium, and admixing the aqueous solution with an appropriate quantity of high surface area carrier substrate material. The active form of the catalyst composition is obtained by removal of the water and other volatile components of the admixture, followed by a suitable drying procedure under high vacuum.

The 5-sulfoisophthalic acid component is employed in a quantity between about 0.5–40 weight percent, and preferably between about 5–30 weight percent, based on the total weight of the catalyst composition.

The catalyst carrier component is selected from substrate materials which have a surface area between about 1–1000 $m^2$/gram, and preferably between about 100–800 $m^2$/gram.

Illustrative of carrier substrate materials are silica, alumina, silica-alumina, magnesia, zirconia, bentonite, crystalline aluminosilicate, activated charcoal, and the like.

The solid catalyst composition can be employed in powder form, or in a compacted form such as granules, beads, pellets, and the like.

The strongly acidic solid catalyst composition of the present invention is suitable for the performance of a broad range of chemical reactions which require conditions of acidic pH. Such reactions include esterification of alcohols with carboxylic acids, hydration of olefins, dehydration of alcohols, transesterification, isomerization, cracking, alkylation, enolether formation, and the like.

In a further embodiment, this invention provides an improved process for producing a carboxylate ester which comprises contacting a mixture of a monoolefin containing between about 2–12 carbon atoms and a carboxylic acid containing between about 1–20 carbon atoms with a strongly acidic solid catalyst at a temperature in the range between about 75°–400° C., wherein said solid catalyst comprises a composite of between about 0.5–40 weight percent, based on catalyst weight, of 5-sulfoisophthalic acid in combination with a carrier substrate having a surface area between about 1–1000 m²/gram. The process may be conducted either batchwise or continuously. The preferred mode of operation is a continuous system in the vapor phase.

The monoolefin and carboxylic acid reactants are employed in a molar ratio between about 1:1 and 50:1, and preferably between about 5:1 and 20:1.

Illustrative of monoolefin reactants are ethylene, propylene, butylene, isobutylene, butene, pentene, hexene, 2-methyl-2-hexene, cyclopentene, cyclohexene, β-pinene, styrene, and the like. Polyolefins such as butadiene and vinylcyclohexene may also be esterified by the invention process. A preferred class of olefins are alkenes containing between about 2–12 carbon atoms.

Illustrative of carboxylic acid reactants are formic acid, acetic acid, chloroacetic acid, trichloroacetic acid, propionic acid, butyric acid, stearic acid, oleic acid, oxalic acid, adipic acid, acrylic acid, methacrylic acid, crotonic acid, maleic acid, cyclohexanecarboxylic acid, benzoic acid, p-chlorobenzoic acid, phenylacetic acid, phthalic acid, isophthalic acid, terephthalic acid, acetylenedicarboxylic acid, and the like. A preferred class of carboxylic acids are alkanoic acids containing between about 1–20 carbon atoms.

The esterification reaction is conducted at a temperature in the range of between about 75°–400° C., and preferably in the range between about 150°–300° C. The pressure of the system can be subatmospheric, atmospheric or superatmospheric, with pressures in the range between about 15 and 1200 psi being preferred.

When the esterification reaction is conducted batchwise, the reaction time may vary in the range between about 0.1–10 hours, depending on the reaction temperature and the other determinants. When the esterification reaction is conducted continuously in the liquid phase, the contact time may vary in the range between about 5–100 seconds. When the esterification is a vapor phase reaction, the contact time may vary in the range between about 0.5–15 seconds, and preferably in the range between about 1–5 seconds.

A liquid phase esterification process can include an inert solvent as a diluent for the reaction medium, e.g., cyclohexane, dioxane, tetrahydrofuran, benzene, carbon tetrachloride, and the like. In the case where the carboxylate ester product is a liquid under the conditions of the esterification reaction, the said carboxylate ester product can be employed as a diluent component.

If the esterification reaction is being conducted in the vapor phase, the feed stream may include an inert gas diluent such as nitrogen, helium, argon, gaseous alkanes, and the like.

The esterification process of the present invention is uniquely efficient because of the high activity and selectivity, and the stability and long service life exhibited by the novel catalyst composite of 5-sulfoisophthalic acid and carrier substrate. It is an important aspect of the present invention esterification process that optimal long term stability and reactivity of the catalyst is achieved only when water is present in the reaction system. Hence, it is highly preferred that the said esterification reaction system contains between about 0.05–1 mole of water per mole of carboxylic acid reactant that is present.

The product mixture recovered from the esterification process is separated into its individual components by conventional procedures, and any unreacted monoolefin and carboxylic acid reactants, or any solvents and the like, can be recylced in an appropriate manner.

The following examples are further illustrative of the present invention. The reactants and other specific ingredients are presented as being typical, and various modifications can be devised in view of the foregoing disclosure within the scope of the invention.

EXAMPLE I

This example illustrates the preparation of a supported 5-sulfoisophthalic acid catalyst.

A 25 gram quantity of 5-sulfoisophthalic acid mono sodium salt was dissolved in water and passed through an ion exchange column (H+ form; Rexyn 101, Fisher Scientific) to convert the sulfonic acid salt to the free sulfonic acid.

The solution was concentrated in vacuo, and the resultant yellow paste-like solid was dissolved in ethanol. The solution was admixed with 100 grams of high surface area silica gel (Davison 408, 720–760 m²/gram). The ethanol was removed from the admixture, and the resulting solid was dried under high vacuum to yield a catalyst consisting of 13 weight percent 5-sulfoisophthalic acid on silica gel.

EXAMPLE II

This example illustrates the vapor phase conversion of propionic acid to ethyl propionate.

A tube reactor (0.5 inch O.D.) was loaded with 25 cubic centimeters of a supported 5-sulfoisophthalic acid catalyst (12–28 mesh) prepared in accordance with the procedure of Example I.

The catalyst zone was heated to a temperature of 190° C., and a vapor phase feed stream was passed continuously through the reactor. The feed mixture consisted of ethylene, propionic acid and water at partial pressures of 191, 11 and 6 psia, respectively.

A propionic acid conversion of 35–40 percent was maintained over a period of 155 hours, with a STY in the range of 106–137 grams/liter hour. The ethylene conversion was about 2.5 percent. The ethylene selectivity to ethyl propionate was consistently at least 95 percent, and the propionic acid selectivity to ethyl propionate was quantitative.

What is claimed is:

1. A strongly acidic solid catalyst composition comprising a composite of between about 0.5–40 weight percent, based on catalyst weight, of 5-sulfoisophthalic acid in combination with a carrier substrate having a surface area between about 1–1000 m²/gram.

2. A catalyst composition in accordance with claim 1 wherein the carrier substrate is silica gel.

3. A catalyst composition in accordance with claim 1 wherein the carrier substrate is alumina.

4. A catalyst composition in accordance with claim 1 wherein the carrier substrate is crystalline aluminosilicate.

* * * * *